US006958243B2

(12) United States Patent
Larhed et al.

(10) Patent No.: US 6,958,243 B2
(45) Date of Patent: Oct. 25, 2005

(54) ORGANIC REACTIONS WITH CO GENERATING MATERIALS

(75) Inventors: Mats Larhed, Uppsala (SE); Mathias Alterman, Stockholm (SE); Yiqian Wan, Uppsala (SE); Hallberg Anders, Uppsala (SE); Nils-Fredrik Kaiser, Uppsala (SE)

(73) Assignee: Biotage AB, Uppsala (SE)

( * ) Notice: Subject to any disclaimer, the term of this patent is extended or adjusted under 35 U.S.C. 154(b) by 225 days.

(21) Appl. No.: 10/014,562

(22) Filed: Dec. 14, 2001

(65) Prior Publication Data

US 2002/0161266 A1 Oct. 31, 2002

Related U.S. Application Data

(60) Provisional application No. 60/255,143, filed on Dec. 14, 2000.

(51) Int. Cl.[7] .......................... G01N 33/00; G01N 33/20
(52) U.S. Cl. .......................... 436/128; 436/73; 436/76; 436/84; 436/127; 435/DIG. 34
(58) Field of Search .............................. 436/35, 55, 73, 436/76, 84, 127, 128; 560/208, 233; 568/454, 451; 556/18, 21; 435/DIG. 34

(56) References Cited

U.S. PATENT DOCUMENTS

| 4,279,722 A | 7/1981 | Kirkbride |
| 5,215,634 A | 6/1993 | Wan et al. |
| 5,411,649 A | 5/1995 | Roussy et al. |

FOREIGN PATENT DOCUMENTS

| EP | 0 742 189 A1 | 11/1996 |
| EP | 0 787 526 A2 | 8/1997 |

OTHER PUBLICATIONS

Corey et al., "Base–Catalyzed Carboxylation of Organic Halides by Nickel Carbonyl in Protic Media", 1969, JACS, 91(5):1233–1234.*
Brunet et al., "Sunlamp–Irradiated Phase–Transfer Catalysis. 1. Cobalt Carbonyl Catalyzed SRN1 Carbonylations of Aryl and Vinyl Halides", 1983, J. Org. Chem., 48(8):116–1171.*
Zoeller et al., "Molybdenum Catalyzed Carbonylation of Ethylene to Propionic Acid and Anhydride", 1997, Catalysis Today, 36(3):227–241.*
Lidstrom et al., "Microwave Assisted Organic Synthesis—A Review", Nov. 5, 2001, Tetrahedron, 57(45):9225–9283.*
Shriver, D.F., Atkins, P.W., Langford, C.H. "Inorganic Chemistry", Oxford University Press (1990), ISBN:0–19–855231–9, p. 512.
Varshavsky et al., J. Organomet. Chem., vol. 31, No. 1 (1971) pp. 119–122.
Grushin et al., Organometallics, vol. 12 (1993) pp. 3846–3850.
Ishiyama et al., Tetrahedron Letters, vol. 34, No. 47 (1993) pp. 7595–7598.
Corey et al., J. American Chem. Soci., vol. 91, No. 5 (1969) pp. 1233–1234.
Caldirola et al., Organometallics, vol. 14 (1995) pp. 3897–3900.
Perrin et al., *Purification of Laboratory Chemicals*, 3rd ed., (1988) Pergamon Press Inc., Terrytown, New York.
Lee et al., Synthetic Communications, vol. 30, No. 23 (2000) pp. 4241–4245.
Schnyder et al., J. Org. Chem., vol. 66 (2001) pp. 4311–4315.
Beller et al., J. Mole. Catalysis, vol. 104A (1995) pp. 17–85.
Soderberg, Transition Metal Alkyl Complexes: Oxidative Addition and Insertion, West Virginia University, Morgantown, WV, pp. 241–259.
Xiao et al., J. Org. Chem., vol. 64 (1999) pp. 2080–2084.
Jayasree et al., Organic Letters, vol. 2, No. 2 (2000) pp. 203–206.
Ie et al., J. Org. Chem., vol. 65 (2000) pp. 1475–1488.

* cited by examiner

*Primary Examiner*—Padmashri Ponnaluri
*Assistant Examiner*—My-Chau T Tran
(74) *Attorney, Agent, or Firm*—Birch, Stewart, Kolasch & Birch, LLP (57) ABSTRACT

The present invention is drawn to a method of performing a one-pot organic reactions including carbon monoxide as reactant, without the use of an external CO gas source, wherein a reaction mixture containing a solid or liquid CO releasing compound, a non-metal substrate and a metal catalyst is exposed to an energy source to release carbon monoxide from the CO releasing compound and wherein carbon atoms of the released carbon monoxide form a bond with the non-metal substrate compound. The present invention is further drawn to a method of preparing chemical libraries and a kit for organic reactions.

30 Claims, 6 Drawing Sheets

FIG.1

FIG.2A

Microwave-assisted palladium-catalyzed amidation utilizing in situ generated carbon monoxide from Mo(CO)$_6$.

Microwave-assisted palladium-catalyzed generation of p-methyl benzoic acid from tolyl iodide utilizing in situ generated carbon monoxide from [Mo(CO)$_6$].

[a]Average isolated yields from 2-3 runs (0.23 mmol scale, SmithSynthesizer™, >95% by GC/MS). [b]p-Methyl-benzoic acid. Ethylene glycol was added as co-solvent.

| entry, aryl-X | R-group | nucleophile | product | yield[a] (%) |
|---|---|---|---|---|
| 1, 1a | MeO- | n-BuNH$_2$ | 2a | 70 |
| 2, 1a | Me- | n-BuNH$_2$ | 2b | 71 |
| 3, 1a | F$_3$C- | n-BuNH$_2$ | 2c | 75 |
| 4, 1a | Ac- | n-BuNH$_2$ | 2d | 77 |
| 5, 1a | MeO- | Piperidine | 2e | 65 |
| 6, 1a | Me- | Piperidine | 2f | 66 |
| 7, 1a | F$_3$C- | Piperidine | 2g | 74 |
| 8, 1a | Ac- | Piperidine | 2h | 83 |
| 9, 1a | Me- | Benzyl amine | 2i | 48 |
| 10, 1b | MeO- | n-BuNH$_2$ | 2a | 69 |
| 11, 1b | Me- | n-BuNH$_2$ | 2b | 72 |
| 12, 1b | F$_3$C- | n-BuNH$_2$ | 2c | 78 |
| 13, 1b | Ac- | n-BuNH$_2$ | 2d | 79 |
| 14, 1b | MeO- | Piperidine | 2e | 66 |
| 15, 1b | Me- | Piperidine | 2f | 69 |
| 16, 1b | F$_3$C- | Piperidine | 2g | 75 |
| 17, 1b | Ac- | Piperidine | 2h | 76 |
| 18, 1b | Me- | Water | 3 | 87[b] |

FIG.2B

**4-Acetyl-*N*-*n*-butyl-benzamide (2d).** White crystals. $^1$H NMR (19 °C, TMS): δ7.90 (d, 2H; Aryl), 7.77 (d, 2H; Aryl), 6.4 (bs, 1H; CONH), 3.39 (q, 2H; N-CH$_2$), 2.45 (s, 3H; COCH$_3$), 1.54 ppm (m, 2H; CH$_2$), 1.33 (m, 2H; CH$_2$), 0.89 (t, 3H; CH$_3$); $^{13}$C NMR (CDCl$_3$, 25 °C, TMS): δ197 (CO), 166 (CONH), 138,9 (C-ipso), 138,7 (C-ipso), 128 (C-HAryl), 127 (CHAryl), 40 (C-aliphatic), 31 (C-aliphatic), 27 (C-aliphatic), 20 (C-aliphatic), 14 (C-aliphatic). MS (70 eV): m/z (%): 219 (10) [M$^+$], 177 (25), 147 (100). Elemental Analysis: Calculated for C$_{13}$H$_{17}$NO$_2$: C, 71.2; N, 6.4; H, 7.8; Found: C, 71.6; N, 6.3; H, 7.9.

4-Trifluoromethylphenyl-piperidin-1-yl-methanone (2g). Yellow oil. $^1$H NMR (19 °C, TMS): δ7.66 (d, 2H; Aryl), 7.48 (d, 2H; Aryl), 3.75 (bs, 2H; CH$_2$), 3.32 (bs, 2H; CH$_2$), 1.67 (bs, 4H; CH$_2$), 1.52 (bs, 2H; CH$_2$); $^{13}$C NMR (25 °C, TMS): δ 168 (CO), 140 (C-ipso), 131 (q; CF$_3$), 127 (CHAryl), 126 (CHAryl), 122 (C-ipso), 49 (broad, C-aliphatic), 43 (broad, C-aliphatic), 27 (broad, C-aliphatic), 26 (broad, C-aliphatic), 24 (C-aliphatic). MS (70 eV): m/z (%): 256 (80) [M+-1], 173 (100), 145 (75). Elemental Analysis: Calculated for C$_{13}$H$_{14}$F$_3$NO × ½H$_2$O: C, 58.6; N, 5.3; H, 5.7; Found: C, 58.8; N, 5.1;

FIG. 3

Type III

Wilkinsons catalyst
Mo(CO)$_6$ / NaH
Diglyme:Ethylene glycol
Smith Synthesizer (170°C x 8 min)

GC-Yield: 8%

FIG. 4

Mo(CO)$_6$, Pd/C
DIEA
Diglyme
Microwaves 1a-c   2a-d   3a-f

| | R1 | | R2 | Time (s) | Conversion of 1[a] | Isolated Yields (%) of 3 | |
|---|---|---|---|---|---|---|---|
| 1a | 4-OMe | 2a | -nBu | 300 | 90% | 3a | 75% |
| 1b | 2-Me | 2a | -nBu | 300 | Full | 3b | 46% |
| 1a | 4-OMe | 2b | -tBu | 900 | Full | 3c | 38% |
| 1a | 4-OMe | 2c | -CH$_2$Ph | 900 | b | 3d | 36% |
| 1a | 4-OMe | 2d | -CH$_2$CH$_2$Si(Me)$_3$ | 900 | Full | 3e | 65% |
| 1c | 4-CF$_3$ | 2d | -CH$_2$CH$_2$Si(Me)$_3$ | 900 | Full | 3f | 65% |

[a]Measured with GC-MS on crude products. [b]not detected with GC-MS.

FIG.5

| Number | Structure | Name |
|---|---|---|
| 3a | | Butyl-4-methoxybensoate |
| 3b | | Butyl-4-methylbensoate |
| 3c | | t-Butyl-4-methoxybensoate |
| 3d | | Bensyl-4-methoxybensoate |
| 3e | | (2-trimethylsilanylethyl)-4-methoxybensoate |
| 3f | | (2-trimethylsilanylethyl)-4-trifluoromethylbensoate |

FIG.6

ORGANIC REACTIONS WITH CO GENERATING MATERIALS

This application claims priority on provisional Application No. 60/255,143 filed on Dec. 14, 2000, the entire contents of which are hereby incorporated by reference.

FIELD OF THE INVENTION

The present invention relates to the use of a material generating CO in situ as a non-catalysing precursor of carbon monoxide in one-pot organic reactions, such as carbonylation and hydroformylation reactions. The material regenerating CO in situ liberates the carbon monoxide into solution upon exposure of the reaction medium to a form of energy and results in the covalent bond formation between the carbon of the carbon monoxide with a non-metal substrate. The present invention further relates to microwave assisted reactions using a non-catalysing material generating CO in situ as a non-catalysing precursor of carbon monoxide so as to result in the covalent bond formation between the carbon of the carbon monoxide with a non-metal substrate. The use of microwave energy in carbon monoxide insertion reactions in combination with a non-catalysing condensed precursor of carbon monoxide provides a means of preparing chemical libraries via combinatorial chemistry.

BACKGROUND OF THE INVENTION

Carbon monoxide is a very versatile and common reagent in organic synthesis. Apart from its common use as reducing agent, several metal-catalysed carbonylative applications have been developed during the last 50 years.

In these reactions, gaseous CO is frequently used as the CO source. A catalyst "shuttles" CO from the gas phase to the substrate where a CO molecule is inserted to said substrate. The catalyst must have certain properties in order to shuttle CO(g). The catalyst should have a spontaneous affinity for CO; otherwise it will not bond to it.

The gaseous carbon monoxide source is conventionally used in reactions such as (a) palladium-catalysed carbonylations of aryl halides to an carboxylic acid or ester with water or an alcohol or to an amide with an amine; (b) metal-catalysed three component cross-coupling reactions between an arylmetal reagent, carbon monoxide gas and an aryl halide, often at high pressures to avoid side products (e.g. direct coupling); and (c) metal catalysed hydroformylation reactions. Still other methodologies (for example Ishiyama et al, *Tetrahedron Letters*, 1993, 34, 7595) resolve cross-reactivity problems by derivatizing the nucleophile or electrophile.

Figure 1:
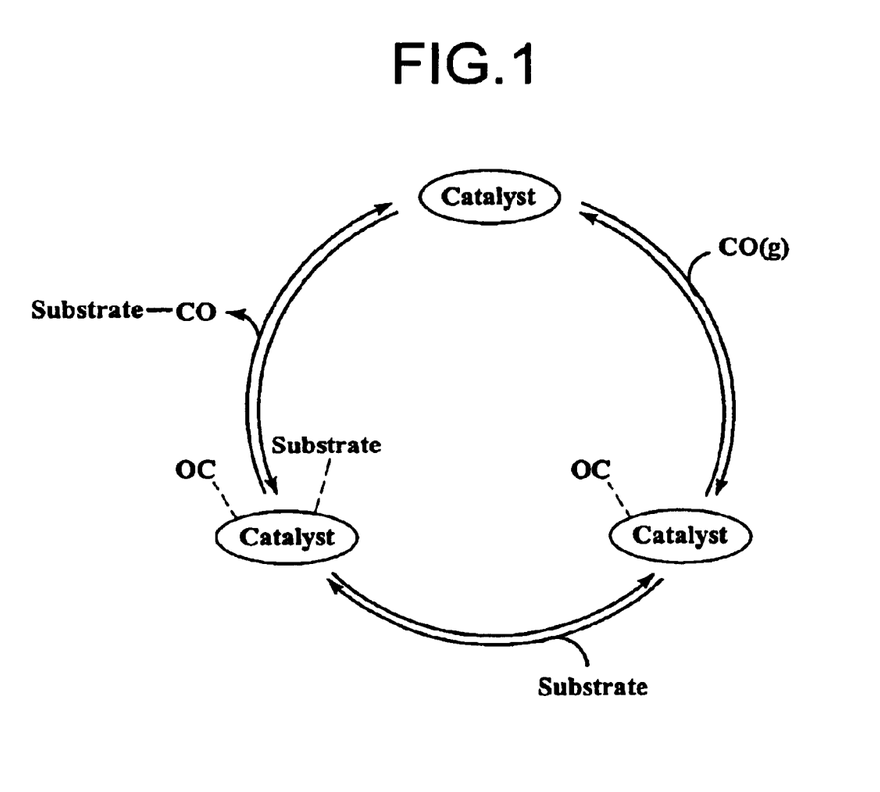

In one conventional method of performing carbonylation reactions, one starts with a metal carbonyl as a pre-catalyst (which by its very existence affirms the affinity of the metal for CO). In broad terms, the following sequence unfolds: irradiation by UV-light or thermal heating makes one CO dissociate from the metal carbonyl pre-catalyst liberating a free site on the metal; the substrate inserts itself to said free-site; a CO molecule originally bonded to the metal inserts to the substrate; the (carbonylated) product is eliminated generating two free sites; these sites are refilled with one new substrate molecule and CO from the gas phase; the cycle repeats itself until the CO or the substrate is fully consumed, or the catalyst is inactivated by, for example, poisoning. A schematic mechanism for these reactions is illustrated in FIG. 1.

In 1969, Corey (Corey E. J., Hegedus, L. S., *Journal of the American Chemical Society*, 1969, 91(5), 1233–1234) published early seminar work on the carboxylation of certain activated substrates (organic halides) with $Ni(CO)_4$ as catalyst and CO-source. Nickel carbonyl is extremely toxic and is a very inefficient catalyst. In fact, 600% metal carbonyl catalyst is required for the reaction to proceed. The reactions were base catalysed and relied on the tendency of metal carbonyls to form more electropositive anionic species under basic conditions. These conditions are appropriate exclusively for only a small number of activated systems. Moreover, the use of an external pressure of carbon monoxide gas, even at high pressures, does not improve the efficiency of the catalyst since the external carbon monoxide retards the formation of free sites on the metal Ni.

A recent methodology for carbonylation reactions, hydrocarbonylation reactions or carbonylation cross-coupling reactions (Johansson et al, *Organometallics*, 1995, 14, 3897) relied on pre-forming a complex between the CO-source and the substrate. This method is limited in that it requires the pre-formation of the metal carbonyl complex with a substrate as well as the pre-activation of said substrate.

It is known that DMF decomposes into carbon monoxide and dimethylamine when heated, cf. e.g. Perrin, D. D., Aremarego, W. L. F. and Perrin, D. R., "*Purification of Laboratory Chemicals*", 3rd, Pergamon Press, 1988, pp. 157–158. DMF has also been used for dimethylamination of acid chlorides, cf. Lee, W. S., Park, K. H. and Yoon, Y.-J., "*Synthetic Communications*" 30(23), pp. 4241–4245 (2000).

In a recent article (Schnyder, A., Beller, M., Mehltretter, G., Nsenda, T., Studer, M. and Indolese, A. F., *J. Org. Chem.* 2001, 66, 4311–4315 an aminocarbonyl reaction for preparation of primary amides is described. In said aminocarbonylation reaction carbon monoxide gas is used as the CO source and reactions with formamide and dimethyl formamide in the presence of imidazole as the base are described. The highest yields were obtained at temperatures between 90 and 120° C. while at higher temperature (150° C.) nonidentified side products were formed. It is also underlined that CO is a pre-requisite for the formation of aroyl species and that the reaction does not proceed without a CO atmosphere. Different bases were also tested and the fastest reactions were obtained with 4-(dimethylamino) pyridine (DMAP) and 4-pyrrolidinopyridine. A high yield was also obtained with imidazole.

SUMMARY OF THE INVENTION

The present invention relates to a method for performing a one-pot organic reaction which includes carbon monoxide as a reactant without the use of an external CO gas source, which comprises preparing a reaction mixture containing a non-catalysing, solid or liquid, i.e. non-gaseous, CO releasing compound generating CO in situ; and exposing said reaction mixture to an energy source affording liberation of carbon monoxide from said non-catalysing CO releasing compound, wherein carbon monoxide is involved in said reaction such that the carbon of said carbon monoxide is involved in bond formation to a non-metal during said organic reaction.

A one-pot reaction in this context means addition of all starting materials, reactants and catalyst(s) before the start of the reaction by exposure to an energy source such as heating or microwaves.

The invention further relates to a method for performing microwave-assisted reactions comprising the steps of preparing a reaction mixture comprising a non-catalysing, non-gaseous compound releasing CO in situ; and exposing said reaction mixture to sufficient microwave energy to afford liberation of carbon monoxide from said non-catalysing compound releasing CO in situ, wherein the carbon monoxide is involved in said reaction such that the carbon of said carbon monoxide is involved in bond formation to a non-metal during said organic reaction.

The invention further relates to method of preparing chemical libraries comprising the steps of preparing a reaction mixture comprising a non-catalysing, solid or liquid CO compound releasing CO in situ, a non-metal substrate compound and a metal catalyst; and exposing said reaction mixture to an energy source affording liberation of carbon monoxide from said non-catalysing compound releasing CO in situ, wherein carbon monoxide is involved in said reaction such that the carbon of said carbon monoxide is involved in bond formation to a non-metal during said organic reaction.

A suitable non-catalysing solid compound releasing CO in situ is a metal carbonyl of the general formula I $$M_x(CO)_y \qquad\qquad\qquad I$$

wherein M is a metal, x is an integer and y is an integer.

A suitable non-catalysing liquid compound releasing CO in situ which is suitable in the method according to the present invention is a formamide of the general formula II $$HCONR_1R_2 \qquad\qquad\qquad II$$

wherein $R_1$ and $R_2$ independently can be H, optionally substituted, linear or branched alkyl, aryl or alkylaryl.

The present invention further relates to a kit for organic reactions having CO as reactant which include a one or more solid or liquid CO releasing compounds, selected from metal carbonyls of the general formula I, $$M_x(CO)_y$$

wherein M is a metal, x is an integer, y is an integer, or formamides of the general formula II, $$HCONR_1R_2$$

wherein $R_1$ and $R_2$ independently can be H, or an optionally substituted, linear or branched alkyl, aryl or alkylaryl group. The reagents of the kit will be placed into a container or containers (e.g. a vial, test tube, reagent bottle, etc) either alone, or if appropriate, with other ingredients. One or more of these containers which contain the reagents for practicing the invention can be placed into an outer container (e.g. a box). The kit may contain instructions for using the reagents and in particular may contain instructions for carrying out a method according to the present invention.

DESCRIPTION OF THE INVENTION

Carbonylation induces a polar A-C(O)—B link between a scaffold and the substituent. By the choice of CO-derivative (e.g. C(O)—B, B=OR ester) the polarity can be tuned to fit the specific requirements and by the choice of substituents (A,B) the spatial arrangement can be tuned. An amide (a type of carbonyl), for instance, is highly stable, possess similarity to biological systems, and are able to participate in hydrogen bonding as both a donor and/or acceptor.

Thus, in addition to the obvious structural changes to a molecule upon carbonylation, many physical attributes can be altered by carbonylation. In medicinal chemistry and in the construction of a biologically active agents in general, one must consider not only the spatial or electrostatic specific interaction with the targets, but also the administration, distribution, metabolism and elimination of the compound. Highly polar substances do not readily pass through the epithelium to enter the blood stream whereas lipophilic compounds have low solubility and tend to accumulate in the liver where they are destroyed. Carbonylation, by introducing a polar —C(O)— unit, substituent (A,B) or apolar substituent (A,B) may serve to tune the polarity of an agent in order to improve its bioavailabilty, its activity and even its specificity. The present method thus serves as a powerful tool for the field of medicinal chemistry as well as in the fields of agrochemistry, food chemistry, colour chemistry and fragrance/flavour chemistry.

Advances in combinatorial chemistry relate to improved methods of handling as well as to improved techniques in performing a chemical reaction. In its applications, the focus is commonly placed on easy or automated handling of a large amount of samples rather than to inert precautions. The development of fast, reliable and convenient protocols is therefore important in the field of combinatorial chemistry. Chemical libraries may be prepared through the emerging field of combinatorial chemistry. The method of the present invention is very amenable to the field of combinatorial chemistry and to the preparation of chemical libraries.

For clarity purposes, it is best to explain at this stage that carbon monoxide acts as an electrophile in these types of reactions. At the start of a reaction, the substrate acts as an electrophile and the catalyst acts as a nucleophile (once activated). However, once the substrate-catalyst complex is formed, the substrate component of the complex acts as a nucleophile to carbon monoxide.

The present invention provides a method of performing organic reactions such as carbonylation reactions, hydrocarbonylation reactions, hydroformylation reactions, carbonylation cross-coupling reactions such as cycloaddition reactions as well as reactions based on similar chemical principles with at least one advantage of allowing for flexibility in selecting the carbon monoxide source from CO releasing compound independently from selecting a reagent such as the nucleophile.

This methodology is surprisingly applicable to a variety of reaction types providing similar or better yields to conventional methodology. Moreover, typically less side products are formed thus facilitating purification. In accordance with the present invention relatively high yields of the desired reaction can be achieved in a short period of time. In some difficult reactions yields of 35% or higher or 50% or higher are considered "high". In other easier reactions yields as high as 80% or greater or 90% or greater and approaching 100% can be achieved.

The liquid or solid material generating CO in situ serves as the source of carbon monoxide. This offers a further advantage of avoiding the use of pressurised cylinders to generate the gas thus offering a pragmatic advantage to conventional methods. The present invention has as an object the use of a CO releasing compound in organic reactions.

Critically, the method according to the present invention is a one-step process. This compares favourably to other methodologies not using gaseous carbon monoxide, wherein the 3-step process of complexation of the metal carbonyl to a reagent, carbonylation, and decomplexation of the reaction mixture, usually via photolysis, is typically required (supra or Johansson et al, *Organometallics*, 1995, 14, 3897).

The present invention has overcome the trouble of using gas in organic reactions such as carbonylations by applying a CO releasing compound, such as the metal carbonyl $M_x(CO)_y$ or the formamide $HCONR_1R_2$, which upon perturbation liberates enough gas in situ for the reaction to take place.

Moreover, the toxicity associated with the handling of CO has been overcome by the convenient method of the present invention.

The term "optionally substituted", in connection with the terms "aryl", "heteroaryl", "cycloalkyl", "heterocyclyl", "alkyl", "alkoxy", "alkenyl", "olefin" and "alkynyl", is intended to mean that the group in question may be substituted one or several times, such as 1 to 5 times, or 1 to 4 times, preferably 1 to 3 times, with a "substituent", namely with one or more groups selected from $C_{1-6}$-alkyl, $C_{1-6}$-alkoxyl, oxo (which when present may be represented in the tautomeric enol form), carboxyl, amino (which when present may be represented in an imine-enamine tautomeric form), hydroxyl (which when present maybe represented in an enol system may be represented in the tautomeric keto form), halogen, such as per- or polyfluorinates, nitro, sulphono, sulphanyl, $C_{1-6}$-carboxyl, $C_{1-6}$-alkoxycarbonyl, $C_{1-6}$-alkylcarbonyl, formyl, aryl, aryloxy, aryloxycarbonyl, arylcarbonyl, heteroaryl, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, or per- or polyfluorinated analogues thereof. The reactivity of the substituents may be attenuated or masked by the use of protective groups known the person skilled in the art.

The term "alkyl" is intended to mean a linear, cyclic (cycloalkyl) or branched saturated hydrocarbon group having from one to twelve carbon atoms, such as methyl, ethyl, n-propyl, isopropyl, cyclopropyl, n-butyl, isobutyl, sec-butyl, tert-butyl, cyclobutyl, pentyl, isopentyl, neopentyl, cyclopentyl, hexyl, cyclohexyl, heptyl, cycloheptyl, and so forth. The term "alkyl" is also intended to mean alkoxy groups such as $C_{1-6}$-alkyl-oxy such as methoxy, ethoxy, n-propoxy, isopropoxy, n-butoxy, isobutoxy, sec-butoxy, tert-butoxy, pentoxy, isopentoxy, neopentoxy, hexoxy and heptoxy. The term "alkyl" is also intended to mean "heterocyclyl" wherein a ring comprising three-, four-, five-, six- seven-, and eight-saturated carbon atoms together with from 1 to 3 heteroatoms form said ring. The heteroatoms are independently selected from oxygen, sulphur, and nitrogen.

Examples of typical "heterocyclyl" groups are 2H-thipyran, 3H-thipyran, 4H-thipyran, tetrahydrothiopyran, 2H-pyran, 4H-pyrane, tetrahydropyran, piperidine, 1,2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2-oxathiin, 1,2-oxathiane, 4H-1,3-oxathiin, 1,3-oxathiane, 1,4-oxathiin, 1,4-oxathiane, 2H-1,2-thiazine, tetrahydro-1,2-thiazine, 2H-1,3-thiazine, 4H-1,3-thiazine, 5,6-dihydro-4H-thiazine, 4H-1,4-thiazine, tetrahydro-1,4-thiazine, 2H-1,2-oxazine, 4H-1,2-oxazine, 6H-1,2-oxazine, 2H1,3-oxazine, 4H-1,3-oxazine, 4H-1,4-oxazine, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,2-dioxole, 1,2-dioxolane, 1,3-dioxole, 1,3-dioxolane, 3H-1,2-dithiole, 1,2-dithiolane, 1,3-dithiole, 1,3-dithiolane, isoxazoline, isoxazolidine, oxazoline, oxazolidine, thiazoline, thiozolidine, 3H-1,2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2,3-trioxolane. 1,2,4-trioxolane, 1,2,3-triazoline and 1,2,3-triazolidine.

The term "aryl" is intended to mean a carbocyclic or heterocyclic aromatic ring (heteroaryl) or ring system. Moreover, the term "aryl" includes fused ring systems wherein at least two aryl rings, or at least one aryl and at cyloalkyl ring share at least one chemical bond. Examples of "aryl" rings include optionally substituted phenyl, naphthalenyl, phenanthrenyl, anthracenyl, acenaphthylenyl, tetralinyl, fluorenyl, indenyl, indolyl, coumaranyl, coumarinyl, chromanyl, isochromanyl, and azulenyl. A preferred aryl group is phenyl.

A heteroaryl or heteraromatic ring is intended to mean an aryl where one or more carbon atoms in an aromatic ring have been replaced with one or more heteroatoms selected from the group comprising nitrogen, sulphur, and oxygen. Furthermore, in the present context, the term "heteroaryl" comprises fused ring systems wherein at least one aryl ring and at least one heteroaryl ring, at least two heteroaryls, at least one heteroaryl and at least one heterocyclyl, or at least one heteroaryl and at least one $C_{3-8}$-cycloalkyl share at least one chemical bond, such as two chemical bonds.

Examples of heteroaryl rings may be selected from the group comprising of optionally substituted, such as mono-, di-, tri-, or tetra-substituted furanyl, thiophenyl, pyrrolyl, phenoxazonyl, oxazolyl, thiazolyl, isothiazolyl, imidazolyl, pyrazolyl, isoxazolyl, imidazolyl isothiazolyl, oxadiazolyl, furazanyl, triazolyl, thiadiazolyl, piperidinyl, pyridinyl, pyridazinyl, pyrimidinyl, pyrazinyl, pyrazolyl and triazinyl, isoindolyl, indolinyl, benzofuranyl, benzothiophenyl, benzopyrazolyl, indazolyl, benzimidazolyl, benzthiazolyl, purinyl, quinolizinyl, quinolinyl, isoquinolinyl, cinnolinyl, phthalazinyl, quinazolinyl, quinoxalinyl, naphthyridinyl, pteridinylthienofuranyl, carbazolyl, acridinyl, phenazinyl, phenothiazinyl, phenoxazinyl and thianthrenyl.

The term "olefin" or "alkenyl" is intended to mean a linear, cyclic, or branched hydrocarbon group having from two to eight carbon atoms wherein at least two said carbons are linked via a double bond. Examples of $C_{2-8}$-alkenyl groups include olefins such as allyl, homo-allyl, vinyl, crotyl, butenyl, pentenyl, hexenyl, heptenyl and octenyl. Examples of $C_{2-8}$-alkenyl groups with more than one double bond include butadienyl, pentadienyl, hexadienyl, heptadienyl, hexatrienyl, heptatrienyl and octatrienyl groups as well as branched forms of these.

Examples of cyclic olefins include cyclopropene, cyclobutene, cyclobutadiene, cyclopentene, cyclopentadiene, cyclohexene, 1,3-cyclohexadiene, 1,4-cyclohexadiene, cycloheptene, 1,2-cycloheptadiene, 1,3-cycloheptadiene, 1,4-cycloheptadiene and 1,3,5 cycloheptatriene.

The terms "alkyne", "propargylic" and "alkynyl" are intended to mean linear, cyclic or branched hydrocarbon groups containing from two to eight carbon atoms wherein at least two said carbons are linked via a triple bond. Examples of $C_{2-8}$-alkynyl groups include acetylene, propynyl, butynyl, pentynyl, hexynyl, heptynyl and octynyl groups as well as branched forms of these.

The term "alkynyl" is also intended to mean enynes, such as conjugated enynes, wherein an olefin and alkyne are linked by a single carbon bond.

The term "halogen" includes fluorine, chlorine, bromine and iodine and is also intended to mean per- or polyfluorinated sulfonated esters.

The method according to the present invention is applicable to a variety of reaction types known to the person skilled in the art as well as to substrates not considered by conventional methodologies to be very amenable to carbonylation reactions. The method of the present invention relates to all reactions wherein CO forms a bond to the substrate as known to the skilled artisan, such as those reviewed in Beller et al, Progress in hydroformylation and carbonylation reactions, *Journal of Molecular Catalysis A*, 1995, 104, 17–85 and in *Transition Metal Alkyl Complexes: Oxidative Addition and Insertion*, Soderberg, B. C., *Comprehensive Organometallic Chemistry II*, Hegedus, L. S. Volume Ed. Abel, E. W.; Stone, F. G. A.; Wilkinson, G. Eds.; Pergamon Press: Oxford 1995; vol. 12, pp. 259.

In the method of the invention, when using the metal carbonyl compound as the CO source the metal carbonyl is not pre-complexed with or bonded to the non-metal to which the carbon of carbon monoxide bonds to during the reaction prior to preparing said reaction mixture.

Typical reaction types, wherein the present method is anticipated to be applicable, are furthermore illustrated by the non-limiting series of reaction types I–VI:

Type I

Type I reactions involve carbonylation of an activated substrate such as an aryl (Ar), such a phenyl, benzyl, or heteroaryl; an alkyl such as $C_{1-12}$-alkyl; an alkenyl, such as $C_{2-12}$-alkenyl; or an alkynyl group such as $C_{2-12}$-alkynyl, each of which may be optionally substituted and each of which is activated with X which may be, for example, halogen, mesylate, triflate, phosphonate, phosphine (in the substrate form of $[ArPPh_3]^+$), tosylate, diazo, —$NH_2$ (which is in situ diazoated), hypervalent iodine, or boronic acid.

In this reaction type, the carbonylation occurs at the activated carbon. The term "activated" is intended to mean that the carbon atom of the substrate with which the carbon atom of carbon monoxide bonds to during the reaction, shares, at the onset of the reaction, a bond with a group or atom which has a higher bond dissociation energy than a carbon-hydrogen bond.

For clarity purposes, it is best to re-state that in these types of reactions, the aryl-X or alk-X acts as an electrophile, the Pd-catalyst is a nucleophile (once activated). However, once the Ar—Pd—X is formed, the Ar or alk is nucleophilic and the Pd is electrophilic. Carbon monoxide acts as an electrophile.

In addition to the examples listed above which serve to activate the substrate, the activating group may be an epoxide or an aziridine. In such cases, the product is typically the corresponding lactone or β-lactam, respectively.

In relation to the nucleophile, R and R' may be independently selected from the group comprising of hydrogen, alkyl, aryl, heteroaryl, alkenyl and alkynyl, each of which may be optionally substituted.

In the embodiment where ROH is the nucleophile, and ROH is water (i.e. R is hydrogen), the product is the carboxylic acid.

These 3-component reactions (i. CO; ii. ArX or alk-X; iii. nucleophilic specie) may be intramolecular. That is to say that the nucleophilic specie and the activated substrate are each moieties of a single molecule.

In intermolecular reactions, i.e. where the organic reactant and the activated substrate are not moieties of a single molecule, the reaction mixture also contains an additional reactant. Suitable additional reactants are selected from the group consisting of amines, alcohols, thiols, hydride ions, alkenes, alkynes, boric acids, boronic acids, carboxylate ions, malonate-type ions, enolate-type ions, azide ions, cyanide ions, halide ions, phosphines $R_3P$ wherein R is aryl, heteroaryl or alkyl, metal organic compounds.

Furthermore, in addition to the examples listed above which serve to activate the substrate, X may be hydroxyl, such that the substrate is a primary, secondary, or tertiary alcohol (Chaudhari et al, *Organic Letters*, 2000, 2 (2), 203). In such embodiments, a halide promoter and/or an acid promoter may additionally be required. A halide promoter may be Li-halide (Chaudhari et al, 2000) wherein the corresponding halo derivative is a reaction intermediate.

Within this embodiment, water may be used as the nucleophile, in which case the corresponding carboxylic acid is the product. An alcohol, thiol, or amine may suitably be used as nucleophile so as to provide an ester, thioester, or amide, respectively.

Alternatively, in the suitable embodiment wherein X is hydroxyl, the hydroxyl may be converted in situ to its corresponding mesylate, triflate, phosphonate, tosylate, or boronic acid using methods known to the person skilled in the art.

The catalyst is typically a catalyst involving $Pd^0/Pd^{II}$ or $Pd^{II}/Pd^{IV}$ catalytic cycles such as conventional neutral palladium complexes such as $PdCl_2(PPh_3)_2$ or cationic complexes such as $Pd(PPh_3)_2(OTs)_2$ or $[Pd(PhCN)_2(PPh_3)_2][BF_4]_2$. The catalyst may alternatively be a palladium(II) complex containing chelating anionic pyridine-2-carboxylato and labile tosylato ligand such as the catalyst described by Chaudhari et al.

Type II

Type II reactions are intended to anticipate 3-component reactions involving direct carbonylation (i.e. unactivated systems) of a substituted aryl or optionally substituted heteroaryl and resulting in acylation of said substrate. The aryl may be substituted with a directing group (Dir) so as to direct the regiochemistry of the carbonylation. The directing group may be, for example, an oxazoline, oxazine, thioazine or pyridine group (Murai et al, *J. Org. Chem.*, 2000, 65, 1475). The directing group may also be an imine so as to form an optionally substituted benzaldehyde imine. The product formed therefrom may serve as an intermediate in intramolecular aldol-type reactions. In some selected examples where the aryl group contains heteroatoms no directing group is needed.

The aryl ring may be a heteroaryl. In a suitable embodiment, the carbonylation may involve the direct carbonylation (of a C—H bond; unactivated system) of heteroaryl, without the use of a directing group. Quite obviously, the heteroaryl may also be substituted with a directing group.

An olefin other than ethylene may also be used, as may trimethylvinylsilane, as the nucleophile. The olefin may be an optionally substituted $C_{2-8}$-alkenyl.

The catalyst used in Type II reactions is typically Pd, V, Pt, Ru, and Rh and suitable precatalysts are $Pd(OAc)_2$, $(PPh)_3RhCl$ (Wilkinson's catalyst), $Ru_3(CO)_{12}$, $[RhCl(coe)_2]_2$, $RuH_2(CO)(PPh_3)_3$ and $Cp*Rh(C_2H_3SiMe_3)_2$.

Type IIIa

Type IIIa reactions involve hydroformylations such as asymmetric hydroformylations. The metal-catalyst is typically selected from the group consisting of Pd, Pt, Rh, Ni, Cu, Cd, Zn, Ti, Sr, Ir, Co, and Ru, preferably selected from Pd, Pt, Rh, Ir, Co, Ru, and Ni, most preferably in this reaction Type, the metal-catalyst selected is Rh, Ir, and Co.

The olefin may be of any length and may be optionally substituted.

The hydrogen source may be hydrogen gas or may be a solid source of $H_2$. One suitable embodiment of this reaction type involves the use of "solid $H_2$" wherein a reagent comprising a weakly acidic proton (such as for example ethanol) and a hydride source are added to the reaction media. An alternative suitable embodiment uses $H_2$ gas and "solid CO" to avoid complexation.

Type IIIb

Type IIIb reactions involve aminomethylation of an olefin. The reaction proceeds via the following process: hydroformylation (IIIa), condensation and hydrogenation.

The olefin may be of any length and may be optionally substituted.

The metal-catalyst in this reaction type is typically selected from the group consisting of Pd, Pt, Rh, Ni, Cu, Cd, Zn, Ti, Sr, Ir, Co, and Ru, preferably selected from Pd, Pt, Rh, Ir, Co, Ru and Ni., most preferably selected from Rh, Ir, and Co.

Water may serve as the reductant in conjunction with CO. Alternatively, hydrogen may be provided. The hydrogen source may be hydrogen gas or may be a solid source of $H_2$. One suitable embodiment of this reaction type involves the use of "solid $H_2$" wherein a reagent comprising a weakly acidic proton (such as for example ethanol) and a hydride source are added to a the reaction media. An alternative suitable embodiment uses $H_2$ gas and "solid CO" to avoid complexation.

Type IVa

In type IVa reactions, R may be an organic species such as an aryl (Ar), such a phenyl, benzyl, or heteroaryl; alkyl such as $C_{1-12}$-alkyl; alkenyl, such as $C_{2-12}$-alkenyl; or alkynyl group such as $C_{2-12}$-alkynyl, each of which may be optionally substituted. The reaction may require a halide promoter and/or an acid promoter (Chaudhari et al, 2000). The product may be a regioisomer of those depicted so as to be the linear acids, esters, amides or thioesters. The use of a halide promoter may reduce reaction times or improve regioselectivity.

The Pd-catalyst is typically a catalyst involving $Pd^O/Pd^{II}$ or $Pd^{II}/Pd^{IV}$ catalytic cycles such as conventional neutral palladium complexes such as $PdCl_2(PPh_3)_2$ or cationic complexes such as $Pd(PPh_3)_2(OTs)_2$ or $[Pd(PhCN)_2(PPh_3)_2][BF_4]_2$. The catalyst may alternatively be a palladium(II) complex containing chelating anionic pyridine-2-carboxylato and labile tosylato ligand such as the catalyst described by Chaudhari.

Type IV(b-h)

$R^1$ may be selected from the group comprising of hydrogen (IVb), optionally substituted alkyl (IVc), optionally substituted aryl (IVd), halogen. (IVe), hydroxyl group (IVf), enamines (IVg), or ethers (IVh).

When the $R^1$ is an alkyl α-substituted with a halogen (IVd), said halogen eliminates, as known to the person skilled in the art. This embodiment (IVd) exemplifies subtypes of reactions wherein $R^1$ is modified during the reaction process.

In IVb type reactions, the nucleophile may, for example, be formic acid, resulting in the formation of the aldehyde.

The metal-catalyst is typically selected from the group consisting of Pd, Pt, Rh, Ni, Cu, Cd, Zn, Ti, or Sr, preferably selected from Pd, Pt, Rh and Ni, most preferably in this reaction type, Pd.

Type V

Type V reactions involve the "anti-Markovnikov" insertion of the carbon monoxide unto propargylic systems to form substituted α,β-unsaturated carbonyls (such as in Alper et al, *J. Org. Chem.*, 1999, 84, 2080). The nature of the substituent depends on the selection of the nucleophile, some of which are shown supra. The product of this reaction is often intermediary and may continue to react such as to cyclise.

The substrate may be an alkynyl of any chain length. The alkynyl may be optionally substituted and $R^1$ may be a substituent as described supra.

The metal-catalyst is typically selected from the group consisting of Pd, Pt, Rh, Ni, Cu, Cd, Zn, Ti, and Sr, preferably selected from Pd, Pt, Rh and Ni, most preferably in this reaction Type, the metal-catalyst is selected from Pd and Rh.

Type VI

Type VI reactions involve the "Markovnikov" carbonylation of conjugated enynes to provide a conjugated diene (such as in Alper et al, *J. Org. Chem.*, 1999, 84, 2080). The catalyst is typically selected from the group consisting of Rh, Pd, Co, Ir and Pt.

All reaction types (I–VI) comprise the steps of preparing a reaction mixture comprising a non-catalysing material generating CO in situ and exposing said reaction mixture to an energy source affording liberation of carbon monoxide from said CO generating material, wherein carbon monoxide is involved in said reaction such that the carbon of said carbon monoxide is involved in bond formation to a non-metal during said organic reaction.

The reaction conditions (e.g. selection of catalyst) shown for each of the reaction types are merely to exemplify an embodiment within the reaction type. The catalyst may be selected from those known in the art. Additives may be required or preferred in embodiments of particular reaction types. The energy source may be tailored to the needs or facilities available to the practitioner.

As stated the metal carbonyl is not complexed with or bonded to a non-metal prior to preparing said reaction mixture. The metal (M) is selected from elements which when bonded to CO, said CO-M bond is typically weaker than C—CO bond in order for the energy barrier for transferring CO to the substrate be favourable. The metal carbonyl is the unique carbonyl source to the reaction mixture and is referred to as CO releasing compound to distinguish it from gaseous sources of CO.

The non-metal substrate can be bound to a polymer. Suitable such polymers are polystyrene, polyacryl amide, polyethylene glycol.

The metal carbonyl, $M_x(CO)_y$ may comprise of transitions elements, Group I, II, III, IV, V, VI; VII or Group VIII metals (M), preferably transition metals and may be tailored to the nature of the reaction, the reagents and/or any catalyst comprising the reaction mixture. Typically, the metal (M) of said metal carbonyl is selected from the group comprising of Mo, Fe, W, Mn, Cr, and Co, preferably Mo, Fe and Cr, most preferably Mo.

The metal carbonyl may exist as a complex of one or more metals complexed with one or more carbon monoxide molecules. Accordingly, in the formula $M_x(CO)_y$, x may be any integer, depending on the level of the complex. Typically, x is selected from 1 to 10 such as 1 to 6, preferably selected from an integer from 1 to 4, such as 1, 2, 3, and 4.

Similarly, y is an integer whose value depends on the size of the metal carbonyl complex. Typically, y is selected from 2 to 40 such as 2 to 24, preferably selected from an integer from 2 to 12. Y is an integer greater than x.

The metal carbonyl may be selected from those known to the person skilled in the art. The metal carbonyl may be selected from the non-limiting group comprising of $Mo(CO)_6$, $W(CO)_6$, $Mn_2(CO)_9$, $Cr(CO)_6$, and $Co(CO)_8$ or derivatives thereof, preferably $Mo(CO)_6$ and $Ca(CO)_6$, especially $Mo(CO)_6$.

Prior to preparing the reaction mixture, the metal carbonyl is not complexed with or bonded to the non-metal with which the carbon of said carbon monoxide is involved in bond formation. This offers the advantage of independently selecting the carbonyl source from the substrate. In a suitable embodiment of the method of the invention, a non-metal ligand may be bonded to the metal carbonyl. However, this not only tends to lower the reactivity of the metal carbonyl but also lowers the capacity of CO-liberation.

The metal carbonyl may comprise of more than one metal so as to form a $(M^1M^2)_x(CO)_y$ complex.

In preferred embodiments, the method comprises the use of from 0.1 to 10,000,000 molar equivalents (higher limit set for PET applications or similar for example) of the metal carbonyl, such as from 0.1 to 1000, 0.25 to 100, 0.5 to 50 or 0.75 to 20 equivalents. Alternatively viewed, the method comprises the use of from 1 to 100 molar equivalents of liberated carbon monoxide. As will be appreciated, the unique stoichiometry of each metal carbonyl (e.g. the x to y ratio in $M_x(CO)_y$) determines the number of equivalents of of complex that is required.

Preferably, the metal-carbonyl is of low toxicity.

The metal carbonyl, when exposed to an energy source, affords liberation of carbon monoxide in its gaseous form from said metal carbonyl, into the reaction mixture.

A suitable non-catalysing compound generating CO in situ which can be used in the method according to the present invention is a formamide of the general formula II $$HCONR_1R_2 \qquad \qquad II$$

wherein $R_1$ and $R_2$ independently can be H, linear or branched alkyl, optionally substituted, aryl or alkylaryl, wherein the alkyl group preferably contains 1 to 6 carbon atoms, such as methyl, ethyl, propyl, isopropyl, butyl, t-butyl, pentyl and hexyl. Each of these alkyl groups may be substituted with a halogen group, such as fluoro. The aryl group is preferably phenyl and a suitable alkylaryl group is ($C_{1-6}$ alkyl) phenyl.

Two examples of suitable formamides of the general formula II are formamide itself, wherein $R_1$ and $R_2$ are H, and dimethyl formamide (DMF), wherein $R_1$ and $R_2$ both are methyl.

When a formamide of the formula II is used in the method according to the present invention as a non-catalysing CO generating compound the reaction mixture in addition also contains imidazole or a substituted imidazole, a metal catalyst and a strong base having a pKa value of about 15 or higher.

The formamide of the general formula II is used in amounts of 0.1 to 10,000,000 molar equivalents, such as from 1 to 1,000, preferably 1 to 100, most preferably 5 to 50 molar equivalents.

Examples of suitable metal catalysts are selected from those stated herein.

Examples of strong bases suitable to use in the reaction mixture together with the amide of formula II in the method according to the present invention are KOtBu, NaOtBu (pKa~17), KO-iso-Pr, NaO-iso-Pr (pKa~16.5), KOEt, NaOEt (pKa~16), KOMe, NaOMe (pKa~15), KOH, NaOH (pKa~16), lithium diisopropylamide (LDA) and NaH (pKa~35).

The energy source serves to provide sufficient energy to liberate a carbon monoxide molecule from the non-catalysing compound generating CO in situ. The method according to the present invention comprises a step of exposing a reaction mixture to a source of energy affording liberation of carbon monoxide. Preferably, when the step of exposing the reaction mixture to an energy source is performed with the metal carbonyl, the reaction mixture comprises the metal carbonyl and the non-metal with which carbon monoxide is involved in bond formation.

In the method of the present invention the energy source is preferably selected from thermal energy, sonic energy, ultraviolet irradiation, microwave energy, and radiofrequency, most preferably thermal energy and microwave energy, particularly microwave energy.

The efficiency of microwave flash-heating chemistry in dramatically reducing reaction times (from days and hours to minutes and seconds) is demonstrated herein. It has been shown useful in other fields of organic chemistry but not in the types of reactions of the present invention. In the context of reactions types discussed herein, it is believed that the use of microwaves will have a tremendous impact on the production rate of substance libraries. Thus, a further aspect of the present invention relates to a method for performing microwave-assisted reactions comprising the steps of preparing a reaction mixture comprising a non-catalysing compound generating CO in situ; and exposing said reaction mixture to sufficient microwave energy to afford liberation of carbon monoxide from said non-catalysing material generating CO in situ, wherein the carbon monoxide is involved in said reaction such that the carbon of said carbon monoxide is involved in bond formation to a non-metal during said organic reaction. The liberating of carbon monoxide is as its gaseous form into said reaction mixture.

Contrary to the case in conventional conductive heating, microwave heat is generated inside the bulk of the sample (in situ heating) and is distributed from inside and out (no wall effects), causing the sample to heat up evenly and rapidly (up to 200° C. per second). Cooling begins as soon as the field is turned off (the reaction vessel is microwave transparent). The homogeneous heating and the sharp difference in temperature profiles between microwave heating and traditional heating can, however, enable convenient high-temperature transformations, result in less decomposition of temperature-sensitive products and in alternative product distributions.

As stated, other fields of chemistry have found advantages of microwave-stimulated reactions. For instance, U.S. Pat. No. 4,279,722 discloses the enhancement of the conversion of liquid hydrocarbons derived from petroleum in a catalytic petroleum refinery process by exposing a mixture of hydrocarbons and catalyst to microwave in the frequency range of about $2.5 \times 10^9$ to $10^{12}$ Hz. U.S. Pat. No. 5,215,634 discloses a process for selectively converting methane and a hydrating agent to $C_3$ oxygenates. In particular, methane is reacted with water in the presence of a nickel metal powder catalyst using microwave irradiation to produce acetone and propanol. U.S. Pat. No. 5,411,649 discloses selective production of ethane and ethylene in high yields by using particular catalysts and microwaves for controlled oxidation. EP 0742189 discloses production of an organo-nitrogen compound by irradiating a mixture of a catalyst, an organic compound and nitrogen with microwaves. Finally, EP 0787526 discloses the enhancement of catalytic reaction rates at low temperatures by utilising microwaves and other techniques, such as simulates boiling, ultrasonication.

In a preferred embodiment of a method of the present invention, the reaction proceeds in a closed vessel such as a SmithProcessVial™ sealed with, for example a Crymper™- seal. A closed vessel has as an advantage of requiring less of the metal carbonyl than an open vial. Nonetheless, in a suitable embodiment of the invention wherein the metal carbonyl compound is used as CO generating material, the reaction proceeds in an open vessel.

In a non-binding interpretation of the mechanism by which the advantages of preferred embodiments of the method of the invention proceed, the temperature and CO-liberation rate seem to have a nearly exponential relationship. That is to say that for low pressure applications (i.e. reactive applications not dependent on high pressures; useful for applications with open vessels) one can have a low temperature (150° C. or below), while for slower reactions, higher temperatures are necessary. Moreover, there are indications that water (and to some extent a coordinating solvent, preferably with high oxygen content) facilitates a smooth liberation of the CO from the metal carbonyl.

Figure 2A:
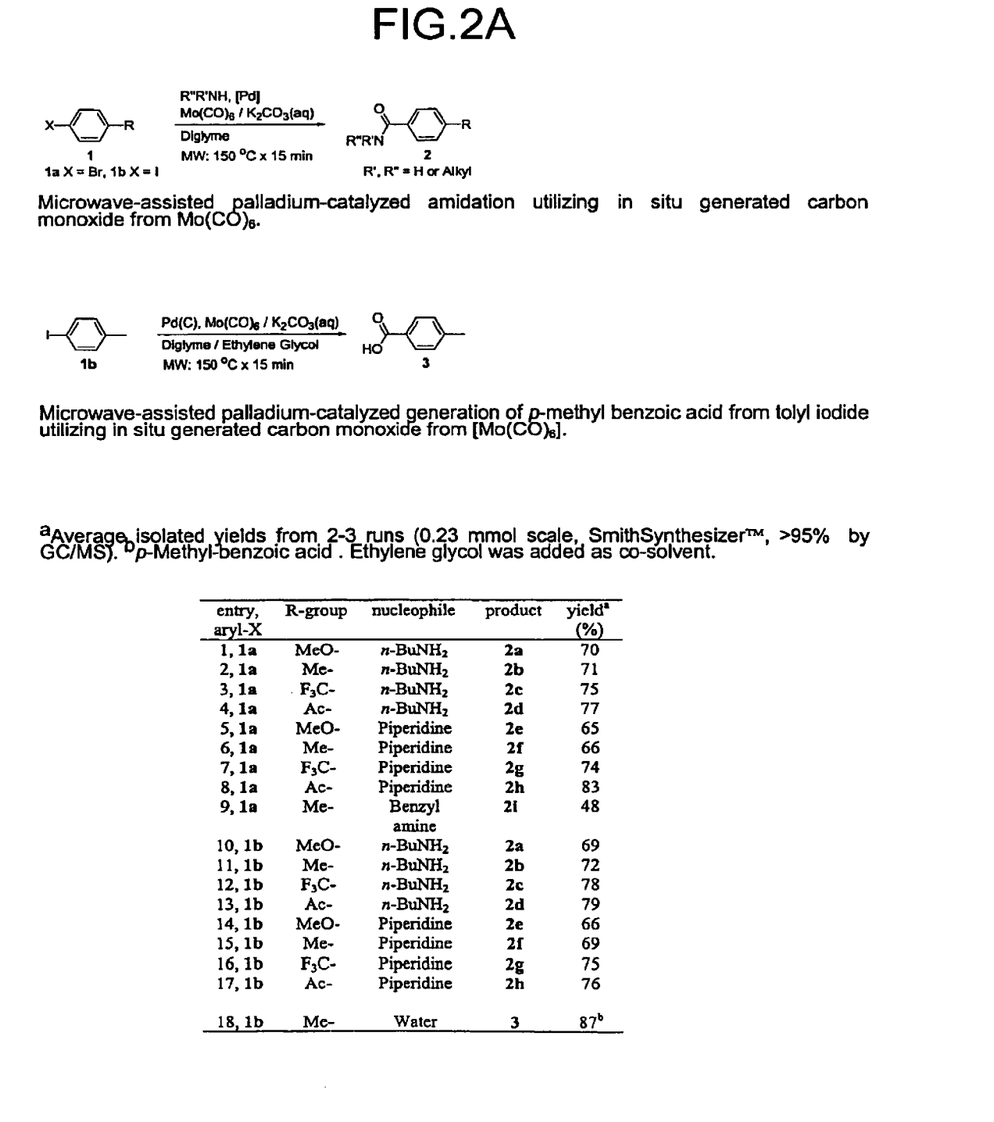
Figure 2B:
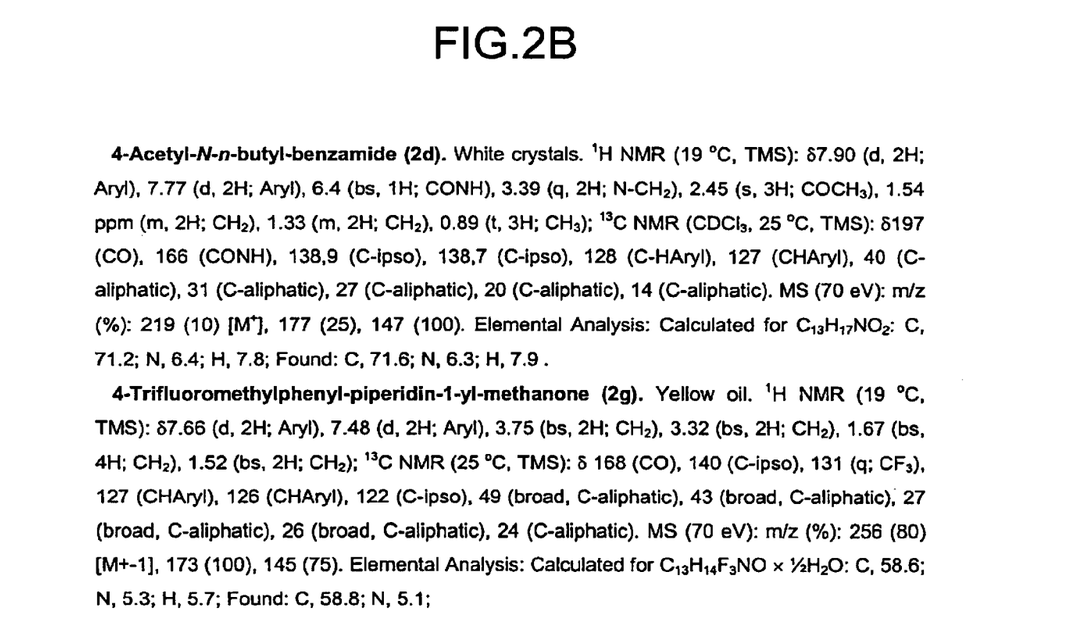

Examples 1 and 2 illustrate that the use of microwave energy in combination with the use of the metal carbonyl as CO generating compound is particularly amenable to at least reaction type I. It is anticipated that microwave energy is amenable to all reaction types of the present invention. FIG. 2 illustrates an example of reaction type I wherein an aryl bromide is carboxylated to an amide or alternatively to a carboxylic acid. FIG. 2 further illustrates the carboxylation of an aryl iodide to its corresponding amide. The CO releasing compound in these illustrative reactions was molybdenum hexacarbonyl. The catalyst, as stated, may be selected from a variety of metal and metal complexes. This is well illustrated in contrasting Example 1 and 2 wherein in the former the highly complexed palladacycle is used whereas in the latter, simple palladium on carbon is used. Full conversion is experienced in all cases. The toluene derivatives, which serve as substrates, are considered to be very difficult substrates by conventional carbonylation methodologies. The positive results shown herein clearly show the advantages of the method of the invention. Less problematic substrates give even better results. The weakly nucleophile aniline has also yielded positive results.

Example 3 illustrates that the use of microwave energy in combination with the use of the metal carbonyl $M_x(CO)_y$ as CO releasing compound is particularly amenable to at least reaction type III and is anticipated to be amenable to all reaction types. Wilkinson's catalyst was found to be a suitable catalyst for the invention.

In the preferred embodiment of the method, wherein microwave energy is used as the energy source, reaction times are typically short. This advantageous feature may be due to the rate at which the temperature of the reaction mixture increase or as a result of putative microwave effects.

Exposure to the microwave energy is preferably for less than 1 hour, preferably for less than 20 minutes.

The temperature of the reaction mixture, upon exposure to the energy source when using a metal carbonyl compound as the CO generating compound must be such that the temperature is raised to at least 50° C., preferably at least 100° C., most particularly to at least 150° C.

In suitable embodiments of the invention, the reaction mixture comprises a metal-carbonyl of the general formula I, a non-metal with which the carbon of CO (of the metal-carbonyl) bonds, and a metal-catalyst. In other suitable embodiments the reaction mixture comprises a formamide of the general formula II, an imidazole or a substituted imidazole, a metal catalyst and a strong base.

The metal catalyst typically comprises of a metal with a ligand and may be as described supra. The ligands, if any, may be selected from the array of ligands known to the person skilled in the art.

The metal is typically selected from Pd, Pt, Rh, Ni, Cu, Cd, Zn, Ti, Sr, Co, Ir, Ru, Ta, W, Fe, Re, or Os, preferably selected from Pd, Pt, Rh, Co, Ir, Ru and Ni.

The metal catalyst is most preferably selected from a $Pd^0$, $Pd^{II}$, $Pd^{IV}$, $Pt^0$, $Pt^{II}$, $Pt^{IV}$, $Ni_0$, $Ni^I$, $Ni^{II}$, $Ni^{III}$, $Rh^0$, $Rh^I$, $Rh^{II}$, $Rh^{III}$, $Co^0$, $Co^I$, $Co^{II}$, $Co^{III}$, $Ir^0$, $Ir^I$, $Ir^{II}$, $Ir^{III}$ species, or of those of approximately the same oxidation state or potential.

The amount of metal catalyst may vary with the reaction type, the reactivity of the substrate, the nature of the metal carbonyl, the energy source, and other reaction conditions such as the solvent and concentration of the reaction mixture. The metal catalyst is typically present in molar equivalents of at most 0.9, such as at most 0.7, preferably at most 0.5, such as 0.4, 0.3, 0.2, 0.1 molar equivalents, most preferably at most 0.05 molar equivalents, such as at most 0.02 or at most 0.01 molar equivalents.

The reaction mixture typically comprises a nucleophilic species. Thus, the reaction mixture may comprise of a non-catalysing compound generating CO in situ, a non-metal with which the carbon of CO bonds, a metal-catalyst, and a electrophilic species. Alternatively, such as in the case of hydroformylation reactions, the reaction mixture may comprise of a non-catalysing compound generating CO in situ, a metal-catalyst, and a non-metal comprising a moiety with which the carbon of CO bonds and a moiety with nucleophilic character. That is to say that the nucleophilic species may be a separate component or may be comprised in the non-metal component. This may vary on whether the reaction comprises an intramolecular coupling step or an intermolecular coupling step.

The present invention has overcome the trouble of using gas in combinatorial chemistry reactions such as carbonylations by applying a compound releasing CO, which upon perturbation liberates enough gas in situ for the reaction to take place. Moreover, the short reaction times associated with the method are further amenable to combinatorial chemistry. Reaction times are particularly significantly reduced when microwave energy is used as the energy source. The non-catalysing compound releasing CO may be selected according to the handling needs and should have low toxicity, such as $Mo(CO)_6$.

The present invention therefore is amenable to the preparation of chemical libraries through the combinatorial chemistry. Thus, the present invention further relates to a method of preparing chemical libraries comprising the steps of preparing a reaction mixture comprising a non-catalysing compound generating CO in situ and exposing said reaction mixture to an energy source affording liberation of carbon monoxide from said CO releasing compound, wherein carbon monoxide is involved in said reaction such that the carbon of said carbon monoxide is involved in bond formation to a non-metal during said organic reaction.

The non-catalysing compound generating CO in situ suitably can be a metal carbonyl of the general formula I or an formamide of the general formula II as described above. In order to provide the great flexibility, it is most preferred that in the area of combinatorial chemistry for the preparation of chemical libraries, the metal carbonyl is not complexed with or bonded to the non-metal (to which CO is inserted) prior to preparing said reaction mixture.

The flexibility, safety, and applicability to various reaction types renders the method particularly amenable to a kit for combinatorial processes. Thus, another aspect of the present invention is a kit comprising a selection of one or more non-catalysing compounds generating CO in situ such as metal carbonyls of formula I or formamides of formula II and/or samples tubes and/or seals ready to use for applying the method of the invention.

The method of the invention is further illustrated by the following examples, which are not intended to limit the scope of the invention.

EXAMPLES

Examples 1–2

Type I: Carbonylation

The reactions and the results of Examples 1 and 2 are shown in FIG. 2.

General Microwave Procedure for the Synthesis of Amides 2. [$Mo(CO)_6$] (30.0 mg, 0.114 mmol) and 1.375 mL of a fresh toluene solution of palladacycle (8.0 mg, 8.5 µmol) and BINAP (14.0 mg, 22.0 µmol), were charged into a Smith Process Vial (a microwave-tube). A teflon-coated stirring bar was added. Utilizing the SmithSynthesizer 0.200 mL 4.0 M $K_2CO_3$(aq), 1.00 mL diglyme, 0.290 mmol amine and aryl halide (0.229 mmol, 0.100 mL of a stock solution of 4.59 mmol aryl halide in 2.00 mL diglyme) were dispensed into the microwave tube. The tube was sealed (Crymper-seal) and the mixture was heated by microwaves at 150° C. for 15 minutes. The mixture turned black during irradiation. After cooling, the reaction mixture was filtrated and concentrated at reduced pressure. The amide 2 was isolated by flash-chromatography.

Instead of the palladacycle and BINAP combination, corresponding amounts of 10% Pd/C (18.1 mg) were used with aryl iodides. $Pd(OAc)_2$ (3.8 mg) performed equally well with aryl iodides.

Note. With Pd/C, an alternative fast, but less efficient way of isolating products 2 (~10–15% lower yields), was to add HCl (2 mL of 2 M concentration) and 3 mL of diethyl ether to the reaction mixture after irradiation. The mixture was shaken once and the ether phase was saved. Evaporation gave pure 2.

Microwave Procedure for the Synthesis of p-Methyl Benzoic Acid 3. [Mo(CO)6] (30.0 mg, 0.114 mmol) and 10% Pd/C (18.1 mg, 17.0 µmol) were charged into a Smith Process Vial (a microwave-tube). A teflon-coated stirring bar was added. Utilizing the SmithSynthesizer 0.200 mL 4 M $K_2CO_3$(aq), 0.700 mL diglyme, 0.300 mL ethylene glycol and p-tolyl iodide (0.229 mmol, 0.100 mL of a stock solution of 1.00 g (4.59 mmol) p-tolyl iodide in 2.00 mL diglyme) were dispensed into the microwave tube. The tube was sealed (Crymper-seal) and the mixture was heated by microwaves at 150° C. for 15 minutes. The mixture turned black during irradiation. Thereafter, 1 mL of 12 M HCl(aq) was added to the reaction mixture. The reaction mixture gets warm! The cold crude acidic mixture was extracted 2–3 times with diethyl ether. The separated diethyl ether phases was subsequently extracted twice with 2 M NaOH(aq). Finally, the carboxylic acid 3 was precipitated by addition of 12 M HCl(aq) to the combined NaOH(aq)-phases and extracted into diethyl ether. Evaporation of the diethyl ether solution afforded pure 3.

Example 3

Figure 3:
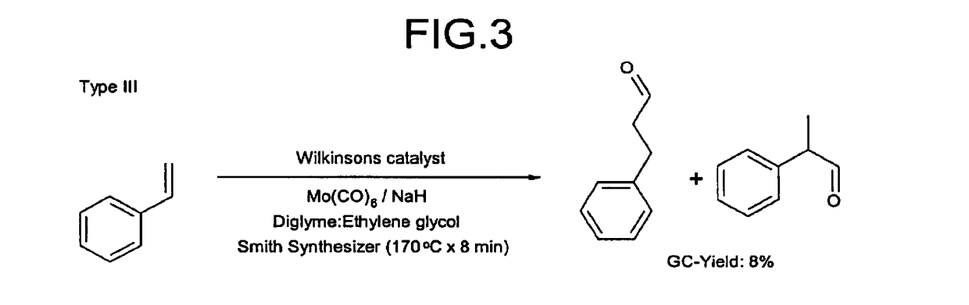

The reaction of Example 3 is shown in FIG. 3.

Type III: Hydroformylation $Mo(CO)_6$ (30 mg, 0.11 mmol), NaH (60%, 16 mg, 0.40 mmol) and Wilkinsons catalyst (10 mg, 11 µmol) were measured into a Smith Processing Vial™ microwave-tube. A teflon-coated stirring bar was added. Utilising the Smith Synthesizer™ styrene (36 ml, 0.31 mmol), 1.200 mL Diglyme and 0.400 mL Ethylene glycol were dispensed into the microwave tube. The tube was sealed (Crymper™-seal). The mixture was subjected to microwaves so that the temperature was 170° C. for 8 minutes. The mixture then turned black. 2 mL of water and 3 mL of ether was added using the Smith Synthesizer™ dispenser. The mixture was shaken and filtrated. Analysis was performed by GC-MS.

Examples 4–9

Figure 4:
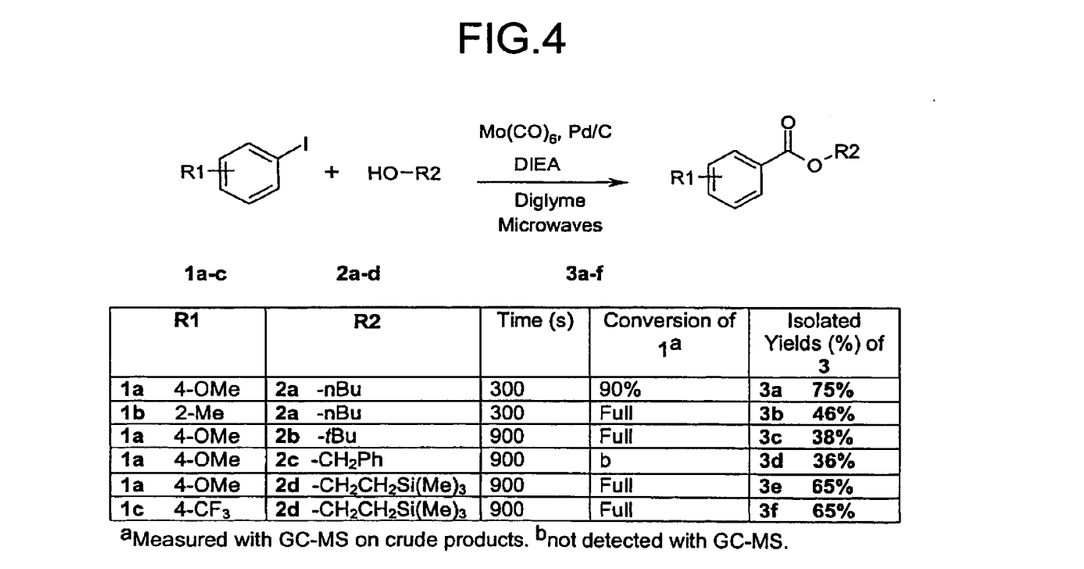
Figure 5:
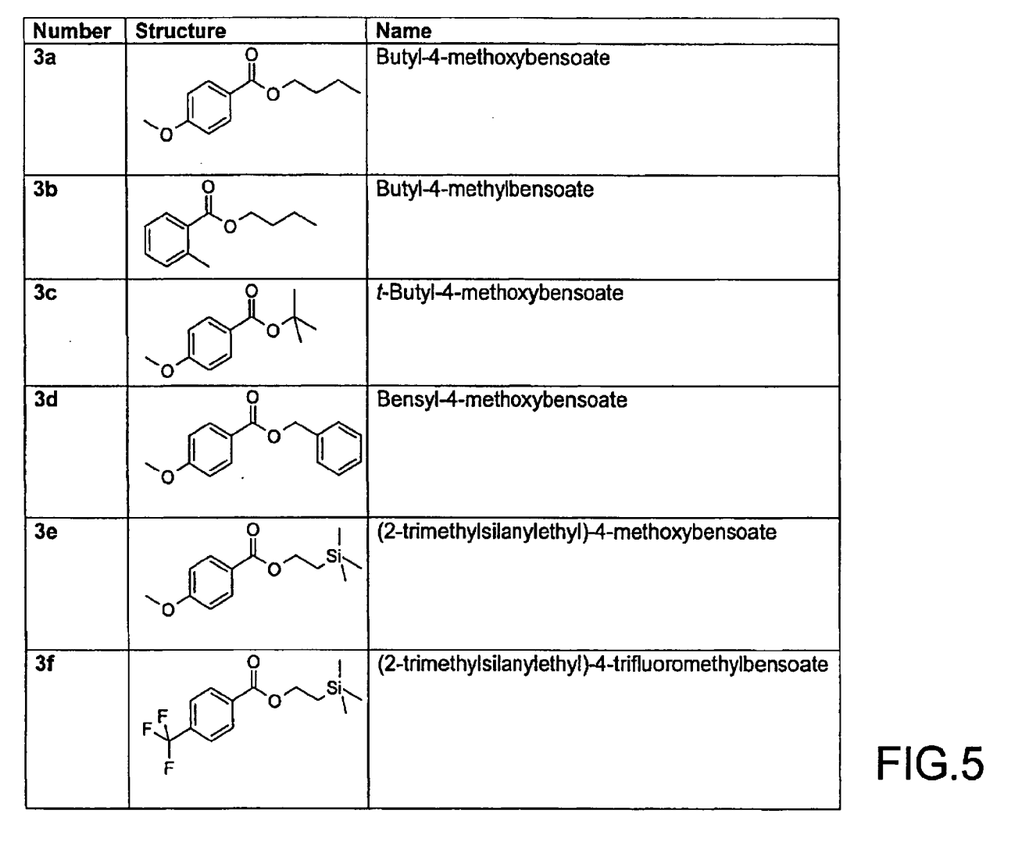

The results and products of Examples 4–9 are shown in FIGS. 4 and 5.

Type I: Carbonylation of Aryl iodides

General Microwave Procedure for the Synthesis of Esters 3.

A SmithProcessingVial™ with a teflon coated stirrer bar was charged with molybdenum hexacarbonyl (33 mg, 0.125 mmol) and palladium on charcoal (12.5 mg, 10% Pd/C). Diglyme (500 µL), diisopropylethylamine (185 µL, 1.0 mmol), alcohol 2 (500 µL, 3.5–6.7 mmol) and aryliodide 1 (0.25 mmol) were thereafter added. The vial was sealed with a Crymper™ seal and the reaction system was mixed manually to a suspension. The reaction was heated by microwave irradiation to 160° C. for 15 min (3a, 3b 5 min) with a Smith Synthesizer™. After cooling, the reaction mixture was evaporated and filtered through a short silica plug with dichloromethane as eluent. Analysis was performed by GC-MS and $^1$H-NMR. The isolated products 3 were >95% pure by capillary GC-MS.

Formamide of the General Formula $HCONR_1R_2$ (II) as CO Generating Compound

Figure 6:
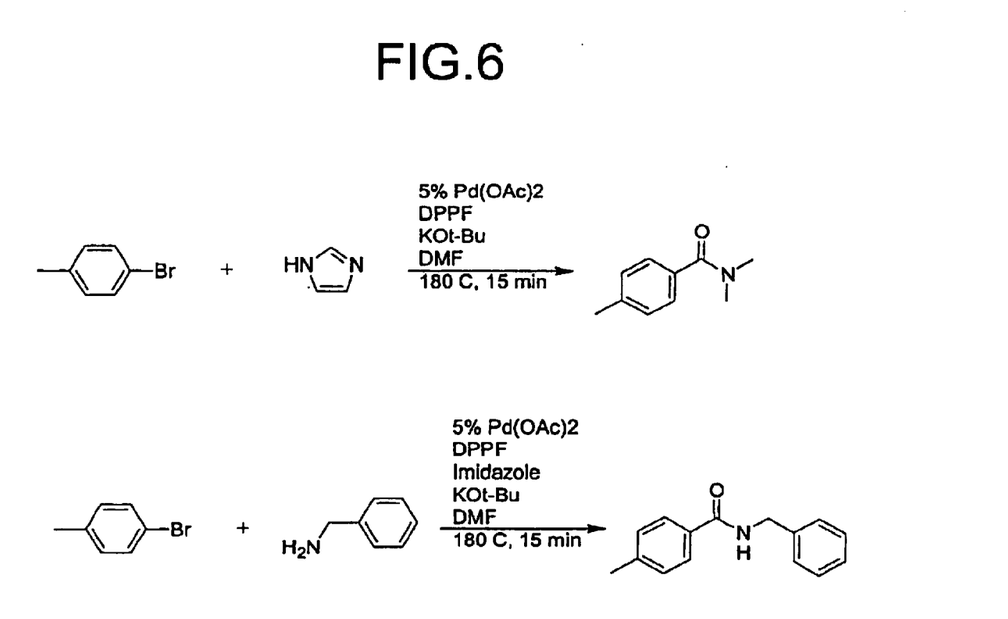

The results and reactions of these examples are shown in FIG. 6 and tables 1–6.

Type I: Carbonylation.

General procedure—A SmithProcessVial™ was charged with 0.75 mmol of bromide, 3 mmol of amine/alcohol, 0.038 mmol of $Pd(OAc)_2$, 0.038 mmol of DPPF, 0.75 mmol of imidazole, 1.13 mmol of potassium tert-butyl oxide and 1 ml of DMF. The reaction mixture was flushed with nitrogen and the cap was tightened thoroughly and then exposed to microwave irradiation for the corresponding time. The reaction tube was allowed to cool to room temperature and the mixture was extracted with 100 ml of ethyl acetate, the organic layer was washed with water (2×50 ml) and brine, dried over potassium carbonate and the solvent was removed under reduced pressure. The residue was purified on silica gel.

The slightly electron rich 4-toluylbromide and the primary benzylamine was used as substrate to investigate the Heck carbonylation reaction with DMF as liquid source of carbon monoxide. The different reagents in the reaction were investigated for their importance for the result (Table 1) and the reaction mixtures were analyzed on GC/MS. First the ligand Dppf was excluded in the reaction (Entry 2). The amide 3 was formed but the pressure in the reaction vessel was too high and the microwave cavity ended the heating prematurely. This is most likely due to the decomposition of the catalyst. Palladium black is formed which have higher susceptibility of microwave irradiation and therefore produce hotspots in the reaction vessel, and the reaction temperature is not controllable. When the imidazole was excluded from the reaction mixture (Entry 3) no carbonylation reaction product was formed. The major product was derived from a Buchwald type amination of the bromide. When the reaction was performed with a weaker base, $K_2CO_3$, no amide product was detected in the reaction mixture and most of the bromide was recovered. Without the palladium catalyst the formamide product of benzylamine was formed as the major product. This product is most likely derived from nucleofilic attack of the amine on DMF (Entry 5). With dimethylacetamide (DMAc) as solvent instead of DMF no carbonylation product was detected (entry 6). In the recent publication by Schnyder et al. they report DMAP as base for decomposition of DMF. When DMAP was used under our condition (entry 7) no desired carbonylation product was yielded, the major product was the resulting secondary amine.

The ligand was shown to be important for the stability of the catalyst in the reaction. Different ligands were screened to optimize the reaction, the results are summarized in Table 2. All the chelating ligands gave the desired product (3) but the mono-dentate ligands were not efficient in this reaction and gave no product. Dppf gave the best result in under these conditions and a yield of 63% of compound 3 was isolated.

In the original reaction 1 eq. of the base KOtBu was used. By increasing the amount to 1.5 eq. the yield could be improved to 73%, but the reaction yield was not improved by further addition of the base (table 3). By lowering the amount of catalyst in the reaction from 5% to 2%, the yield dropped to 47% (Entry 4, Table 3).

The influence of the reaction time and the temperature was investigated and the results are summarized in Table 4. A shorter time gave a lower yield but a more dramatic effect was observed when lowering the reaction temperature. At 150° C. only a very small amount of the product could be isolated. When increasing the temperature to 190° C. a slightly better result was observed.

The pressure of the reaction was monitored during the reactions. A pressure of 1.7 Bar was formed in the sealed vessels after 15 min The origin of the pressure is most likely due to the evaporation of the DMF, although the contribution of the formed $CO_{(g)}$ could not be determined. When heating a sample of pure DMF the Pressure reached 2.2 Bar with the same temperature and time. The higher pressure formed in pure DMF could be that no $CO_{(g)}$ is consumed in this system.

The high temperature required in the reactions, 180–190° C., is easily obtained in the microwave cavity. In a conventional oil-bath this temperature is not so practical. A reaction (table 5 entry 1) was therefor performed with conventional heating at 130° C. but with a longer reaction time, 10 h. This gave the desired product in a moderate yield, 25%.

The scope of the reaction was demonstrated using 5% $Pd(OAc)_2$, 5% Dppf, 1 eq. imidazole, 3 eq. amine, and 1.5 eq. KOtBu in DMF as solvent. A variety of amines and aryl bromides were converted to the corresponding amides, here shown in Table 5. The slightly electron rich 4-bromotoluene was reacted with primary, secondary, and anilinic amines (entries 1–4).

All of the reactions gave a good yield, and surprisingly the secondary amine morpholine gave a very good yield. With out an external amine the dimethyl amide was formed, where the amine part of the amide was provided from the DMF (entry 4). In entry 5 formamide was used as solvent instead of DMF. This gave the unsubstituted amide in good yield (74%). This provides a very convenient method for formation of primary amides without the use of ammonia. The influence of the electronic and steric properties of the aryl bromide was investigated in entry 6–9. With the slightly more steric 2-bromotoluene the reaction needed a longer time for completion, but resulted in an excellent yield (94%). The electron neutral and electron rich bromides, entireties 7,8, both gave good yields, although the 4-methoxybenzyl bromide required 20 min for total consumption of the starting material. When applying the electron deficient 4-cyanobenzyl bromide no desired product was detected in the reaction mixture (entry 9). The secondary amine derived from the competing amination reaction, which is a fast reaction with electron deficient aryl bromides, was the major product in this reaction. In the absence of any bromide the benzylformamide was formed in a good yield, entry 10, this reaction is less likely to be palladium catalyzed.

To further broaden the scope of the reaction a primary alcohol was used in the reaction instead of an amine. The resulting benzyl ester was formed in a good yield (Table 6).

Experimental Section

General considerations—$^1$H and $^{13}$C NMR spectra were recorded at 270.2 and 67.9 MHz, respectively. Chemical shifts are given as δ values (ppm) downfield from tetramethylsilane. Flash column chromatography was performed on silica gel 60 (0.04–0.063 mm). Thin-layer chromatography was performed on precoated silica gel F-254 plates (0.25 mm) and visualized with UV light or ninhydrin in ethanol. The palladium acetate was bought from Merk Company, BINAP from Aldrich, and DPPF from Stream Chemicals Company. All other chemicals were purchased from Aldrich or Fluka and were used directly without further purification. All microwave reactions were carried out in SmithProcessVial. Microwave heating was carried out with Smith creator and Smith Synthesizer from Personal Chemistry. It is not recommended to repeat these reactions in a multimode domestic microwave oven producing no uniform irradiation. GC-MS was performed with a HP-5890 series II equipped with a HP-5971 Mass selective detector, and a HP-1 capillary column using 70–305 ss program gradient.

TABLE 1

Importance of the reagents.

| Entry | Solvent | Pd(OAc)$_2$ | Dppf | Imidazole | Base | Relative Peak height on GC/MS Amide 3 |
|---|---|---|---|---|---|---|
| 1 | DMF | Yes | Yes | Yes | KOtBu | 80 |
| 2 | DMF | Yes | No | Yes | KOtBu | 44[a] |
| 3 | DMF | Yes | Yes | No | KOtBu | 0[b] |
| 4 | DMF | Yes | Yes | Yes | K$_2$CO$_3$ | 0 |
| 5 | DMF | No | Yes | Yes | KOtBu | 0[c] |
| 6 | DMAc | Yes | Yes | Yes | KOtBu | 0 |
| 7 | DMF | Yes | Yes | No (DMAP) | KOtBu | 0[b] |

[a]The pressure of the reaction was to high to control and the reaction was terminated.
[b]The major product was the product derived from amination reaction.
[c]Formylation of the amine was the major product.

TABLE 2

Ligand Screening.

| Entry | Ligand | Isolated Yield |
|---|---|---|
| 1 | Dppf | 63 |
| 2 | Dppp | 37 |

TABLE 2-continued

Ligand Screening.

| Entry | Ligand | Isolated Yield |
|---|---|---|
| 3 | P(o-Tol)$_3$ | — |
| 4 | Binap | 49 |
| 5 | PPh$_3$ | — |

TABLE 3

Amount of Base and Catalyst.

| Entry | Ekv. Base | mol % Pd(OAc)$_2$ | Isolated Yield |
|---|---|---|---|
| 1 | 1 | 5 | 63 |
| 2 | 1.5 | 5 | 73 |
| 3 | 2 | 5 | 70 |
| 4 | 1.5 | 2 | 47 |

TABLE 4

Time and Temperature variation.

| Entry | Time (Min) | Temp (° C.) | Isolated Yield |
|---|---|---|---|
| 1 | 10 | 180 | 53 |
| 2 | 15 | 180 | 73 |
| 3 | 15 | 150 | 3 |
| 4 | 15 | 190 | 76 |

TABLE 5

| Entry | Aryl Bromide | Amine | Product | Time (min) | Temp (°C.) | Isolated Yield (%) |
|---|---|---|---|---|---|---|
| 1 | 4-methylphenyl bromide | benzylamine | N-benzyl-4-methylbenzamide | 15 | 190 | 76 |
| 2 | 4-methylphenyl bromide | aniline | 4-methyl-N-phenylbenzamide | 20 | 190 | 77 |
| 3 | 4-methylphenyl bromide | morpholine | (4-methylphenyl)(morpholino)methanone | 20 | 190 | 83 |
| 4 | 4-methylphenyl bromide | — | N,N,4-trimethylbenzamide | 15 | 180 | 59 |
| 5 | 4-methylphenyl bromide | —[a] | 4-methylbenzamide | 15 | 180 | 74 |
| 6 | 2-methylphenyl bromide | benzylamine | N-benzyl-2-methylbenzamide | 20 | 190 | 94 |
| 7 | phenyl bromide | benzylamine | N-benzylbenzamide | 15 | 190 | 82 |
| 8 | 4-methoxyphenyl bromide | benzylamine | N-benzyl-4-methoxybenzamide | 20 | 190 | 70 |
| 9 | 4-cyanophenyl bromide | benzylamine | N-benzyl-4-cyanobenzamide | 20 | 190 | 0[a] |

TABLE 5-continued

| Entry | Aryl Bromide | Amine | Product | Time (min) | Temp (°C.) | Isolated Yield (%) |
|---|---|---|---|---|---|---|
| 10 | — | H₂N-CH₂-C₆H₅ | HC(O)NH-CH₂-C₆H₅ | 20 | 190 | 67 |

TABLE 6

| Entry | Aryl Bromide | Alcohol | Product | Time (min) | Temp (°C.) | Yield (%) |
|---|---|---|---|---|---|---|
| 1 | 4-Me-C₆H₄-Br | HO-CH₂-C₆H₅ | 4-Me-C₆H₄-C(O)O-CH₂-C₆H₅ | 15 | 190 | 71 |

N-Benzyl-4-methyl-benzamide (entry 1, table 5), With hexane/acetone (4:1) as eluent gave 128.6 mg of the entitled compound as a white solid. IR(neat) ν 1638 cm$^{-1}$; MS m/z 225(M$^+$); $^1$H NMR (CDCl$_3$) δ 7.63 (d, J=8.1 Hz, 2H), 7.27–7.12 (m, 7H), 6.52 (brs, 1H), 4.55 (d, J=5.8 Hz, 2H), 2.31 (s, 3H); $^{13}$C NMR (CDCl$_3$) δ 167.3, 141.9, 138.2, 131.4, 129.2, 128.7, 127.8, 127.5, 126.9, 43.9, 21.4.

4-Methyl-N-phenyl-benzamide (entry 2, table 5), With hexane/acetone (3:1) as eluent gave 122.7 mg of the entitled compound as a white solid. IR (neat) ν 1652 cm$^{-1}$; MS m/z 211(M$^+$); $^1$H NMR (CDCl$_3$) δ7.92 (brs, 1H), 7.78 (d, J=8.1 Hz, 2H), 7.66 (d, J=7.7 Hz, 2H), 7.39–7.11 (m, 5H), 2.41 (s, 3H); $^{13}$C NMR (CDCl$_3$) δ165.7, 142.3, 138.0, 132.0, 129.3, 129.0, 127.0, 124.4, 120.1, 21.5.

4-methyl-N-morpholine-benzamide (entry 3, table 5), With CHCl$_3$/MeOH (35:1) as eluent on aluminaoxide gave 127.5 mg of the entitled compound as a pale yellow liquid which contained 10% of dimehtyl-4methylbenzamide determined by $^1$H NMR. IR (neat) ν 1649 cm$^{-1}$; MS m/z204 (M$^+$); $^1$H NMR (CDCl$_3$) δ 7.17–7.10 (m, 4H), 6.52 (brs, 1H), 3.70–3.08 (m, 8H), 2.22 (s, 3H); $^{13}$C NMR (CDCl$_3$) δ 170.5, 139.9, 132.2, 129.0, 128.8, 127.1, 66.8, 21.1.

N-benzyl-2-methyl-benzamide (entry 6, table 5), With hexane/acetone (3:1) as eluent gave 158.3 mg of the entitled compound as a white solid. IR (neat) ν 1627 cm$^{-1}$; MS m/z 225(M$^+$); $^1$H NMR (CDCl$_3$) δ 7.36–7.11 (m, 9H), 6.24 (brs, 1H), 4.59 (d, J=5.9 Hz, 2H), 2.43 (s, 3H); $^{13}$C NMR (CDCl$_3$) δ 169.9, 130.9, 129.8, 128.7, 127.7, 127.5, 126.6, 125.6, 43.8, 19.8.

N-Benzyl-4-methoxy-benzamide (entry 8, table 5), With hexane/acetone (3:1) as eluent gave 125.7 mg of the entitled compound as a white solid. IR (neat) ν 1632 cm$^{-1}$; MS m/z 241(M$^+$); $^1$H NMR (CDCl$_3$) δ 7.78–7.75 (m, 2H), 7.34–7.28 (m, 5H), 6.90–6.86 (m, 2H), 6.68 (brs, 1H), 4.59 (d, J=5.8 Hz, 2H), 3.81 (s, 3H). $^{13}$C NMR (CDCl$_3$) δ 166.8, 162.1, 138.4, 128.7, 128.6, 127.8, 127.4, 126.5, 113.6, 55.3, 43.9.

Benzyl-4-methylbenzoate (entry 1, table 6), With hexane/acetone (5:1) as eluent gave 120.8 mg of the entitled compound as a colorless liquid. IR (neat) ν 1716 cm$^-$; MS m/z 226(M$^+$); $^1$H NMR (CDCl$_3$) δ 7.99 (d, J=8.2 Hz, 2H), 7.44–7.25 (m, 7H), 5.37 (s, 2H), 2.40 (s, 3H); $^{13}$C NMR (CDCl$_3$) δ 166.5, 143.7, 136.1, 129.7, 129.0, 128.5, 128.1, 128.0, 127.3, 66.5, 21.7.

What is claimed is:

1. A method of performing a one-pot organic reaction, which includes carbon monoxide as reactant without the use of an external CO gas source, comprising
   preparing a reaction mixture containing a non-catalysing solid CO releasing compound which is a metal carbonyl of the general formula I, wherein M is a metal, x is an integer, y is an integer, a non-metal substrate compound and a metal catalyst; wherein the metal carbonyl is not complexed with or bonded to the non-metal substrate compound prior to preparing said reaction mixture; and
   exposing said reaction mixture to an energy source to release carbon monoxide from the CO releasing compound,
   wherein carbon atoms of the released carbon monoxide form a bond with the non-metal substrate compound.

2. The method according to claim 1 wherein the reaction mixture in addition to the non-metal substrate compound also contains an organic reactant.

3. The method according to claim 2, wherein the organic reactant is selected from the group consisting of amines, alcohols, thiols, hydrides, alkenes, alkynes, boric acids, boronic acids, carboxylate ions, malonate-type ions, enolate-type ions, azide ions, cyanide ions, halide ions, phosphines R$_3$P wherein R$_3$ is aryl, heteroaryl or alkyl, metal-organic compounds.

4. The method according to claim 1, wherein M is selected from Mo, W, Mn, Cr, and Co.

5. The method according to claim 1, wherein the metal carbonyl is selected from the group consisting of Mo(CO)$_6$, W(CO)$_6$, Mn$_2$(CO)$_{10}$, Cr(CO)$_6$, and Co$_2$(CO)$_8$ or derivatives thereof.

6. The method according to any claim 1, wherein the metal carbonyl is used in amounts of 0.1 to 10,000,000 molar equivalents.

7. The method according to claim 1, wherein the energy source raises the temperature of the reaction mixture to at least 100° C.

8. The method according to claim 1, wherein the metal catalyst is selected from the group consisting of Pd$^0$, Pd$''$, $Pd^{IV}$, $Pt^0$, $Pt^{II}$, $Pt^{IV}$, $Ni^0$, $Ni^{I}$, $Ni^{II}$, $Ni^{III}$, $Rh^0$, $Rh^{I}$, $Rh^{II}$, $Rh^{III}$, $Co^0$, $Co^{I}$, $Co^{II}$, $Co^{III}$, $Ir^0$, $Ir^{I}$, $Ir^{II}$ and $Ir^{III}$ species.

9. The method according to claim 1, wherein the metal catalyst is present in molar equivalents of at most 0.9.

10. The method according to claim 1, wherein the non-metal substrate compound is covalently bound to a polymer.

11. The method according to claim 1, wherein the energy source is selected from the group consisting of thermal energy, sonic energy, ultraviolet irradiation, microwave energy, and radiofrequency.

12. The method according to claim 4, wherein M is Mo or Cr.

13. The method according to claim 12, wherein M is Mo.

14. The method according to claim 5, wherein the metal carbonyl is $Mo(CO)_6$, or $Cr(CO)_6$.

15. The method according to claim 14, wherein the metal carbonyl is $Mo(CO)_6$.

16. The method according to claim 6, wherein the metal carbonyl is used in amount of 0.1 to 1000 molar equivalents.

17. The method according to claim 16, wherein the metal carbonyl is used in amounts of suitably 0.20 to 100 molar equivalents.

18. The method according to claim 17, wherein the metal carbonyl is used in amounts of 0.25 to 5 molar equivalents.

19. The method according to claim 18, wherein the metal carbonyl is used in amounts of 0.3 to 0.6 molar equivalents.

20. The method according to claim 7, wherein the energy source raises the temperature of the reaction to at least 130° C.

21. The method according to claim 20, wherein the energy source raises the temperature of the reaction to at least 150° C.

22. The method according to claim 9 wherein the metal catalyst is present in molar equivalents of at most 0.5.

23. The method according to claim 22, wherein the metal catalyst is present in molar equivalents of 0.5–0.02.

24. The method according to claim 11, wherein the energy source is preferably thermal energy or microwave energy.

25. The method according to claim 24, wherein the energy source is microwave energy.

26. A method of preparing chemical libraries which comprises performing the one-pot organic reaction of claim 1.

27. The method according to claim 26, wherein the energy source is selected from the group consisting of thermal energy, sonic energy, ultraviolet irradiation, microwave energy, and radiofrequency.

28. The method according to claim 27, wherein the energy source is preferably thermal energy or microwave energy.

29. The method according to claim 28, wherein the energy source is microwave energy.

30. A kit for performing the one-pot organic reaction method of claim 1, comprising a non-catalysing solid CO releasing compound which is a carbonyl of the general formula I, $$M_x(CO)_y$$

wherein M is a metal, x is an integer, y is an integer; and a metal catalyst.

* * * * *